United States Patent [19]

Matsuda et al.

[11] Patent Number: 5,777,094
[45] Date of Patent: Jul. 7, 1998

[54] CDNA OF DOCK180 GENE AND DOCK180 PROTEIN

[75] Inventors: Michiyuki Matsuda; Takeshi Kurata, both of Tokyo, Japan

[73] Assignee: Research Development Corporation of Japan, Saitama, Japan

[21] Appl. No.: 588,985

[22] Filed: Jan. 19, 1996

[51] Int. Cl.$^6$ .................................... C12N 15/12
[52] U.S. Cl. .................... 536/23.5; 435/65.1; 435/252.3; 435/320.1; 435/325; 435/340.1; 530/300; 530/350; 536/23.1
[58] Field of Search ................................ 435/69.1, 252.3, 435/325, 340.1, 320.1; 536/23.1, 23.5; 530/300, 350

[56] References Cited

PUBLICATIONS

Hasegawa et al. (1996) 16:1770–1776.
Matsuda et al. (1996) 271:14468–14472.

*Primary Examiner*—John Ulm
*Assistant Examiner*—Kenneth A. Sorensen
*Attorney, Agent, or Firm*—Wenderoth, Lind & Ponack

[57] ABSTRACT

The present invention provides a cDNA of DOCK180 gene, which has a nucleotide sequence of SEQ ID NO: 1 and of which translation product binds to the proto-oncogene product CRK, a recombinant vector containing this cDNA, a DOCK180 protein expressed from the EDNA which has a amino acid sequence of SEQ ID NO: 2, and an antibody to the DOCK180 protein. According to the present invention, It is possible to develop new diagnosing and therapeutic techniques using DOCK180 protein and antibody against the protein.

6 Claims, 1 Drawing Sheet

CDNA OF DOCK180 GENE AND DOCK180 PROTEIN

BACKGROUND OF THE INVENTION

1. Field of the Invention

The present invention relates to a cDNA of DOCK180 protein, which binds to the proto-oncogene product CRK, a recombinant vector containing this cDNA, a DOCK180 protein expressed from the cDNA, and an antibody to the DOCK180 protein. The cDNA of the present invention, the DOCK180 protein, and the antibody are very useful for diagnosis of tumor cells and development of a cancerocidal method for suppressing tumor cells.

2. Description of Related Art

Recent progress of cellular biology and molecular biology is really remarkable. Active research efforts are being made on carcinogenesis on the genetic level, and such efforts have identified many oncogenes and antioncogenes associated with human. It is also known that various proteins are expressed from these genes.

For example, CRK protein, which is expressed from a proto-oncogene CRK, is one of the major proteins controlling proliferation of higher eukaryote, and is known to regulate proliferation of tumor cells in many malignant tumors.

It has now been revealed that this CRK protein functions through binding to DOCK180 protein. DOCK180 is therefore attracting attention as a diagnostic indicator of tumor cells and as a target for missile therapy using various antitumor agents.

However, because no information has been available about a gene encoding the DOCK180 protein, it has been impossible to effectively utilize this protein widely for diagnosis of cancerous diseases, clarification of carcinogenesis mechanism, or development or a new cancer therapy.

SUMMARY OF THE INVENTION

The present invention has an object to provide a cDNA of DOCK 180 gene and a genotic engineering material permitting easy manipulation of this cDNA and expression of the protein in a large scale.

The present invention has another object to provide a DOCK180 protein which is expressed from the above-mentioned cDNA, and an antibodies against this protein.

The present invention provides a cDNA of the DOCK180 gene, which has the nucleotide sequence defined in Sequence Listing by SEQ ID NO: 1.

Furthermore, the present invention provides a recombinant vector containing the cDNA of DOCK180 gene. More concretely, the present invention provides the plasmid pDOCK180 held by *E. coli* DOCK180 (FERM BP-5362).

The present invention further provides a DOCK180 protein having the amino acid sequence defined in Sequence Listing by SEQ ID NO: 2, and antibodies to DOCK180 protein prepared by using the DOCK180 protein as an antigen.

DETAILED DESCRIPTION OF THE INVENTION

Figure 1:
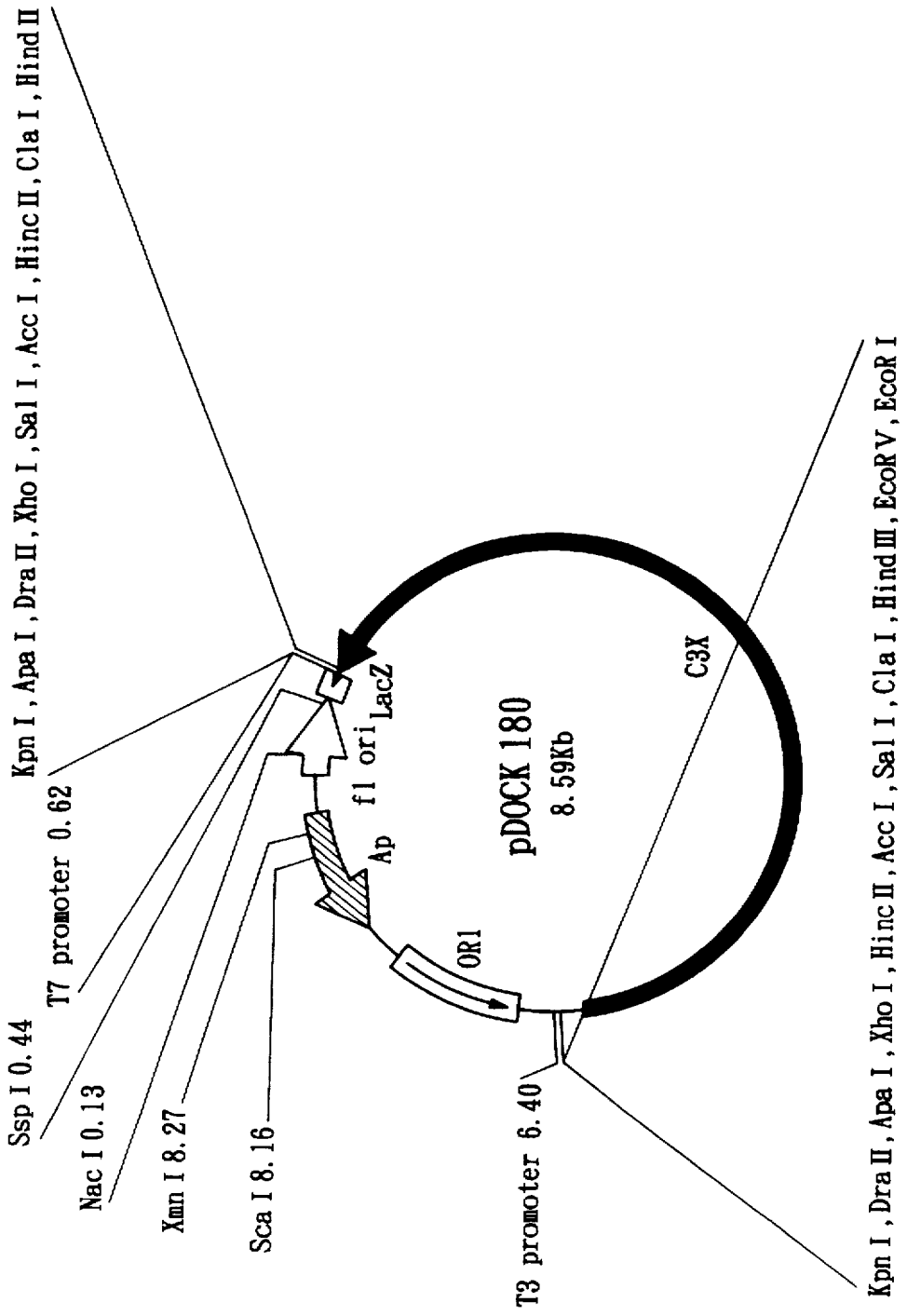
FIG. 1 is a constitutional diagram of pDOCK180, which is a cloning vector of the present invention.

The cDNA of the present invention can be isolated and purified from higher eukaryotes such as cells derived from human, mouse, and chicken by the application of, for example, the method of Sambrook et al.(Molecular Cloning, second edition, Cold Spring Harbor Laboratory, New York, 1989). More specifically, the cDNA can be obtained by purifying mRNA of DOCK180 protein gene from animal cell, and then synthesizing a cDNA chain from the mRNA by the use of reverse transcriptase. From among the thus synthesizable cDNAs of DOCK180 protein, the nucleotide sequence of cDNA derived from human cells and the amino acid sequence of the translation domain thereof are defined in Sequence Listing by SEQ ID NOs: 1 and 2.

Then, the recombinant vector of the present invention can be prepared by inserting a fragment of the resultant cDNA into known cloning vectors. Ligation of the cDNA fragments and the vectors may be accomplished by, for example, the above-mentioned method of Sambrook et al. Preferable vectors include a plasmid and a λ-phage for *Escherichia coli* as the host, and an applicable plasmid is, for example, one derived from pBR322. A preferable λ-phase is λ gt11.

Transfer of the thus prepared recombinant vectors into the host may be conducted through infection by λ-phage as presented in the above-mentioned paper by Sambrook et al. For example, a transformed cells with the recombinant vector containing the above-mentioned cDNA are available by inoculating the recombinant λ gt11 into *Escherichia coli* Y1090 at 37° C.

Selection of a transformed cell may be accomplished by using a known method, depending upon the kind of the cloning vector. For example, selection of a transformed cell with λ gt11 can be performed as follows. The above-mentioned recombinant λ gt11 containing the cDNA can be inoculated into *Escherichia coli* Y1090 under a temperature condition of 37° C., and the *E. coli* cells are cultured on an ager plate containing trypton, yeast extract, NaCl and ampicillin (hereinafter abbreviated as an "agar medium"). Then, a nitrocellulose membrane containing isopropyl thio-D-galactoside (hereinafter abbreviated as "IPTG") is placed on the plate for another several hours to induce transcription from the integrated cDNA. After the binding of an enzyme-labelled CRK protein to the membrane (Matsuda et al., Mol. Cell. Biol., 12: 3482–3489, 1992), an lamda phase plaques having the recombinant vector can be selected by putting a substrate for the enzyme in it. A preferable labelling enzyme is alkaline phosphatase or peroxidase. CRK protein may be manufactured as a fusion protein with glutathione S-transferese (hereinafter abbreviated as "GST"), and selection may be accomplished by using an antibody against this GST.

The cDNA fragment inserted into λ phage can be cleaved out and re-inserted into a plasmid vector, if necessary. An example or recombinant plasmid vector of the invention is pDOCK180 which is prepared by inserting the cDNA of SEQ ID NO: 1 into vector plasmid pBlue ScriptIIKS(+), for which details are presented in Example 2 later. The pDOCK180 was transfected into the XL1-Blue strain derived from *Escherichia coli* K12 strain, and the transformant *E. coli* DOCK180 having the pDOCK180 was deposited to National Institute of Biocience and human Technology, an international depository, under Budapest Treaty as a deposit No. FERM BP-5362 on Jan. 12, 1996.

Then, the DOCK180 protein of the present invention can be exressed from the cDNA of SEQ ID NO: 1. For production of the protein, an expression vector is prepared by inserting the cDNA fragment into a known expression vector. The cDNA fragment can be isolated from the above-mentioned cloning vector, pDOCK180. While there is no particular limitation as to the expression vector, a preferable one is pGEX1, pG5X2T or pGEX3X using *E. coli* as the host. The expression vector containing the cDNA fragment can be introduced into an *Escherichia coli* (for example, DH5 strain derived from *Escherichia coli* K12 strain) by a known method. The DOCK180 protein of the present invention is easily produced in a large scale by culturing the transformed cells. More specifically, a concrete example comprises the stops of culturing the transformed *Escherichia coli* at 37° C. for 3 to 24 hours on L-broth containing ampicillin, bacteriolyzing through ultrasonic blending, and adsorbing this sample to a carrier such as glutathione sephalose (made by Pharmacia P-L Biochemicals Company), thereby isolating and purifying the target DOCK180 protein.

An antibody against DOCK180 protein is available by inoculating the thus purified DOCK180 protein to an animal by a conventional method. Applicable animals include rabbit, mouse, goat, sheep, horse and hamster, and among others, rabbit or mouse is preferable.

The thus obtained anti-DOCK180 protein antibody can be used, for example, for quantitative determination or separation of DOCK180 protein in a sample, and further, serves as a useful material for missile therapy using an antitumor agent with DOCK180 as a target.

The cDNA, the protein and the antibody of the present invention provide various genetic manipulation materials useful for development of a new cancer therapy. These materials include an antisense RNA of DOCK180 gene, a variant protein of DOCK180, and a virus vector which expresses these RNA, variant protein, and anti-DOCK180 protein antibody in tumor cells.

The present invention will be described below in further detail by means of examples. It is needless to mention that the present invention Is not limited in any manner by the following examples.

EXAMPLE 1

A cDNA fragment to human DOCK180 protein gene was isolated and cloned as follows.

An mRNA of DOCK180 gene was isolated from human spleen and a cDNA fragment was synthesized from the mRNA. The cDNA fragment was then integrated into λ gt11, and a recombinant vector thereof was infected to *Escherichia coli* Y1090, which was plated onto LA agar culture medium. After six hours, a nitrocellulose membrane containing 1 mM IPTG was placed on this medium, and after three hours of culture, this nitrocellulose membrane was Incubated for an hour with a phosphate buffer solution (pH: 7.5) containing 2% skim milk and 0.05% Tween 20. Then, after reaction for an hour with a phosphate buffer solution containing 1 μg/ml GST-CRK and 1 μg/ml anti-GST monoclonal antibody, and for an hour with 1 μg/ml alkaline phosphate-labelled anti-mouse antibody (made by TAGO Company), the phage having an ability to bind to CRK protein was identified by means of AP PURPLE (made by Bio Iol Company), a substrate for alkaline phosphatase. This phage was purified through three runs of plaque formation, and then DNA thereof was isolated by the phenol extraction method, and cleaved with a restriction enzyme EcoRI. Next, part of cDNA of DOCK180 gene was prepared through electrophoresis. This cDNA fragment was isotope-labelled with random oligo primer (made by Behlinger Company) and 32P-deoxycytidine triphosphate. With the use of this labelled cDNA, the above-mentioned recombinant λ gt11 with cDNA derived from a human spleen was screened through plaque hybridization by the method of Sambrook et al. (Molecular Cloning, second edition, Cold Spring Harbor Laboratory, New York, 1989), and further six clones of recombinant λ gt11 having DOCK180 protein cDNA were obtained. DNAs of these phages were cleaced with restriction enzyme EcoRI to isolate cDNA of DOCK180 gene and subcloned into phagemid vector pUC119. A single stranded DNA was purified from the thus obtained recombinant vector, and the nucleotide sequence thereof was determined by the use of an automatic nucleotide sequence reader (made by ABI Company). The identified nucleotide sequence thereof is shown in Sequence Listing by SEQ ID NO; 1, and the amino acid sequence of the anticipated translation product, by SEQ ID NO: 2. As a result of retrieval of this amino acid sequence in the database in the GenBank of the European Molecular Biology Laboratories (EMBL), the amino terminal end of DOCK180 protein shares homology with Fyn and Yes of tyrosine kinase by more than 20%. This domain has a structure known as SH3, and is present in various protein groups involved in signal transduction of cell proliferation in addition to that of tyrosine kinase. However, DOCK180 protein was found to be different from any known proteins and to be a new signal transduction factor.

EXAMPLE 2

From the group of recombinant pUC119 obtained in Example 1, the DNA fragments excluding overlapping portions were isolated and ligated each other to prepare a fragment containing all the translation domain of the cDNA. The resultant cDNA fragment was then inserted into the plasmid vector pBlue Script II KS(+) to obtain the recombinant vector pDOCK180. This pDOCK180 has a constitution as shown In FIG. 1.

Further, this cloning vector pDOCK180 was introduced into an XL1-Blue strain derived from *Escherichia coli* K12 to obtain a transformant *E. coli* DOCK180 (FERM BP-5362).

EXAMPLE 3

The cloning vector pDOCK180 obtained by Example 2 was cleaved with a restriction enzyme to prepare a cDNA domain of DOCK180 protein. The resultant cDNA fragment was then inserted into plasmid pGEX1, thereby preparing expression vectors. Transformant cells were prepared by introducing the expression vectors into *Escherichia coli* DH5. After culturing this transformant cells in 1 1 L-broth containing ampicillin up to an absorbance of 0.6, IPTG was added to 0.5 mM, and culturing was continued for another three hours. After collection, the bacteria were ultrasonic-treated to remove crushed pieces of bacteria, and the supernatant was mixed with glutathione sephalose (made by Pharmacia P-L Biochemicals Company). After rinsing glutathione sephalose with a phosphate buffer solution, DOCK180 protein was eluded with the use of a phosphate buffer solution containing 5 mM glutathione. This protein was dialyzed with a phosphate buffer solution, and then a portion thereof was analyzed with SDS-polyacrylamide gel: a GST fused-DOCK180 protein having a purity of over 90% was synthesized.

EXAMPLE 4

The DOCK180 protein purified in Example 3 was subcutaneously inoculated three times to a rabbit, together with complete Freund's adjuvant, and then, serum was sampled.

Reactivity of this serum with the purified DOCK180 protein was investigated by the Western blotting technique:

a clear reactivity was demonstrated with the DOCK180 protein even when diluted to about 1,000. This permitted confirmation of applicability thereof as an antibody against DOCK180 protein.

What is claimed is:

1. A cDNA of a DOCK180 gene which encodes a DOCK180 protein having the amino acid sequence according to SEQ ID NO: 2.

2. A cDNA of a DOCK180 gene, which has a nucleotide sequence according to SEQ ID No: 1, and whose translation product binds to proto-oncogene product CRK.

3. A recombinant vector containing the cDNA as claimed in claim 2.

4. Plasmid pDOCK180, which is inserted in *E. coli* DOCK180 (FERM BP-5362).

5. A purified DOCK180 protein having an amino acid sequence according to SEQ ID NO: 2.

6. A DOCK180 protein having an amino acid sequence according to SEQ ID NO: 2, which is expressed from the cDNA of the DOCK180 gene claimed in claim 2.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 6519 base pairs
( B ) TYPE: nucleic acid
( C ) STRANDEDNESS: single
( D ) TOPOLOGY: linear ( i i ) MOLECULE TYPE: cDNA to mRNA ( i i i ) HYPOTHETICAL:

( i v ) ANTI-SENSE:

( v ) FRAGMENT TYPE:

( v i ) ORIGINAL SOURCE: spleen cell of homo sapiens ( i x ) FEATURE:
( A ) NAME/KEY: CDS
( B ) LOCATION: 24..5619

( x i ) SEQUENCE DESCRIPTION: SEQ ID NO:1:

| | | | | | | |
|---|---|---|---|---|---|---|
| GCACGAGCGG | CTCCGGCGGC | GCCATGACGC | GCTGGGTGCC | CACCAAGCGC | GAGGAGAAGT | 60 |
| ACGGCGTGGC | TTTTTATAAC | TATGATGCCA | GAGGAGCGGA | TGAACTTTCT | TTACAGATCG | 120 |
| GAGACACTGT | GCACATCTTA | GAAACATATG | AAGGGTGGTA | CCGAGGTTAC | ACGTTACGAA | 180 |
| AAAAGTCTAA | GAAGGGTATA | TTTCCTGCTT | CATATATTCA | TCTTAAAGAA | GCGATAGTTG | 240 |
| AAGGAAAAGG | GCAACATGAA | ACAGTCATCC | CGGGTGACCT | CCCCCTCATC | CAGGAAGTCA | 300 |
| CCACGACACT | CCGAGAGTGG | TCCACCATCT | GGAGGCAGCT | CTACGTGCAA | GATAACAGGG | 360 |
| AGATGTTTCG | AAGTGTGCGG | CACATGATCT | ATGACCTTAT | TGAATGGCGA | TCACAAATTC | 420 |
| TTTCTGGAAC | TCTGCCTCAG | GATGAACTCA | AGAACTGAA | GAAGAAGGTC | ACAGCCAAAA | 480 |
| TTGATTATGG | AAACAGAATT | CTAGATTTGG | ACCTGGTGGT | TAGAGATGAA | GATGGGAATA | 540 |
| TTTTGGATCC | AGAATTAACT | AGCACGATTA | GTCTCTTCAG | AGCTCATGAA | ATAGCTTCTA | 600 |
| AACAAGTGGA | GGAAAGGTTA | CAAGAGGAAA | AATCTCAAAA | GCAGAACATA | GATATTAACA | 660 |
| GACAAGCCAA | GTTTGCTGCA | ACCCCTTCTC | TGGCCTTGTT | TGTGAACCTC | AAAAATGTGG | 720 |
| TTTGTAAAAT | AGGAGAAGAT | GCTGAAGTCC | TCATGTCTCT | ATATGACCCT | GTGGAGTCCA | 780 |
| AATTCATCAG | TGAGAACTAC | CTGGTTCGCT | GGTCCAGTTC | AGGATTACCT | AAAGACATAG | 840 |
| ACAGATTACA | TAATTTGCGA | GCCGTGTTTA | CTGACCTCGG | AAGCAAAGAC | CTGAAAAGGG | 900 |
| AGAAAATCAG | TTTTGTCTGT | CAGATTGTTC | GCGTGGGTCG | CATGGAGCTG | AGGGACAACA | 960 |
| ACACCAGGAA | ACTGACCTCG | GGGTTGCGGC | GACCTTTTGG | AGTGGCTGTG | ATGGATGTAA | 1020 |
| CAGATATAAT | AAATGGAAAA | GTAGATGATG | AAGATAAGCA | GCATTTCATT | CCCTTTCAGC | 1080 |
| CGGTGGCAGG | GGAGAATGAC | TTCCTTCAGA | CTGTTATAAA | CAAAGTCATC | GCTGCCAAAG | 1140 |
| AAGTCAACCA | CAAGGGGCAG | GGTTTGTGGG | TAACATTGAA | ATTACTTCCT | GGAGATATCC | 1200 |
| ATCAGATCCG | AAAAGAGTTT | CCGCATTTAG | TGGACAGGAC | CACAGCTGTG | GCTCGAAAAA | 1260 |
| CAGGGTTTCC | GGAGATAATC | ATGCCTGGTG | ATGTTCGAAA | TGATATCTAT | GTAACATTAG | 1320 |
| TTCAAGGAGA | TTTTGATAAA | GGAAGCAAAA | CAACAGCGAA | GAACGTGGAG | GTCACGGTGT | 1380 |

-continued

| | | | | | |
|---|---|---|---|---|---|
| CTGTGTACGA | TGAGGATGGG | AAACGATTAG | AGCATGTGAT | TTTCCCGGGT | GCTGGTGATG | 1440 |
| AAGCGATTTC | AGAGTACAAA | TCTGTGATTT | ACTACCAAGT | AAAGCAGCCA | CGCTGGTTTG | 1500 |
| AGACTGTTAA | GGTGGCCATT | CCCATCGAGG | ACGTTAACCG | CAGTCACCTT | CGGTTTACCT | 1560 |
| TCCGCCACAG | GTCATCACAG | GACTCTAAGG | ATAAATCTGA | GAAAATATTT | GCACTAGCAT | 1620 |
| TTGTCAAGCT | GATGAGATAC | GATGGTACCA | CCCTGCGAGA | CGGAGAGCAC | GATCTTATCG | 1680 |
| TCTATAAGGC | CGAAGCGAAG | AAGCTGGAAG | ATGCTGCCAC | GTACTTGAGT | CTGCCCTCCA | 1740 |
| CGAAGGCAGA | GTTGGAAGAA | AAGGGCCACT | CGGCCACCGG | CAAGAGCATG | CAGAGCCTTG | 1800 |
| GGAGCTGCAC | CATTAGCAAG | GACTCCTTCC | AGATCTCCAC | GCTCGTGTGC | TCCACCAAAC | 1860 |
| TGACTCAGAA | CGTGGACCTT | CTGGGGCTCT | TGAAATGGCG | CTCCAACACC | AGCCTGCTGC | 1920 |
| AGCAGAACTT | GAGGCAGCTG | ATGAAAGTCG | ATGGTGGTGA | AGTAGTGAAG | TTTCTTCAGG | 1980 |
| ACACGTTGGA | TGCCCTCTTC | AACATCATGA | TGGAGAACTC | AGAGAGTGAG | ACTTTTGACA | 2040 |
| CGTTAGTCTT | TGATGCTCTG | GTATTTATCA | TTGGACTGAT | TGCTGATAGA | AAATTTCAGC | 2100 |
| ATTTTAATCC | TGTTTTGGAA | ACTTACATTA | GAAACACTT | TAGTGCAACG | TTAGCCTACA | 2160 |
| CGAAGTTGAC | AAAAGTGTTG | AAGAACTACG | TGGACGGTGC | TGAGAAGCCG | GGAGTAAATG | 2220 |
| AGCAGCTGTA | CAAAGCCATG | AAAGCGCTAG | AATCCATCTT | CAAGTTCATC | GTGCGCTCCA | 2280 |
| GGATCCTGTT | CAATCAACTG | TATGAAAACA | AGGGAGAGGC | TGACTTCGTG | GAATCTTTGC | 2340 |
| TGCAGCTCTT | CAGGTCCATC | AATGACATGA | TGAGCAGCAT | GTCAGACCAG | ACCGTCCGGG | 2400 |
| TGAAGGGGGC | AGCACTGAAA | TACTTACCAA | CGATCGTCAA | CGATGTGAAA | TTGGTGTTTG | 2460 |
| ATCCCAAAGA | GCTCAGCAAA | ATGTTTACTG | AATTCATCCT | CAATGTTCCC | ATGGGCTTGC | 2520 |
| TGACCATCCA | GAAACTCTAC | TGCTTGATCG | AAATCGTCCA | CAGTGACCTC | TTCACACAGC | 2580 |
| ATGACTGCAG | AGAGATCCTG | CTTCCCATGA | TGACCGATCA | GCTCAAGTAC | CATCTGGAGA | 2640 |
| GACAGGAGGA | CCTGGAGGCC | TGCTGTCAGC | TGCTCAGCCA | CATCCTGGAG | GTGCTGTACA | 2700 |
| GGAAGGACGT | GGGGCCAACC | CAGAGGCACG | TCCAGATTAT | CATGGAGAAA | CTTCTCCGGA | 2760 |
| CCGTGAACCG | AACCGTCATT | TCCATGGGAC | GAGATTCTGA | ACTCATTGGA | AACTTCGTGG | 2820 |
| CTTGCATGAC | AGCTATTTTA | CGACAAATGG | AAGATTACCA | TTATGCCCAC | TTGATCAAGA | 2880 |
| CTTTTGGGAA | AATGAGGACT | GATGTGGTAG | ATTTCCTAAT | GGAAACATTC | ATCATGTTTA | 2940 |
| AGAACCTCAT | TGGAAAGAAC | GTTTACCCCT | TCGACTGGGT | GATCATGAAC | ATGGTGCAAA | 3000 |
| ATAAAGTCTT | CCTGCGAGCA | ATTAATCAGT | ATGCAGATAT | GCTGAACAAA | AAATTTCTGG | 3060 |
| ATCAAGCCAA | CTTTGAGCTA | CAGCTGTGGA | ACAACTACTT | TCACCTGGCT | GTTGCTTTCC | 3120 |
| TTACTCAAGA | GTCCCTGCAA | CTGGAGAATT | TTTCAAGTGC | CAAGAGAGCC | AAAATCCTTA | 3180 |
| ACAAGTACGG | AGATATGAGG | AGACAGATTG | GCTTTGAAAT | CAGAGACATG | TGGTACAACC | 3240 |
| TTGGTCAACA | CAAGATAAAG | TTCATTCCAG | AAATGGTGGG | CCCAATATTA | GAAATGACAT | 3300 |
| TAATTCCCGA | GACGGAGCTG | CGCAAAGCCA | CCATCCCCAT | CTTCTTTGAT | ATGATGCAGT | 3360 |
| GTGAATTCCA | TTCGACCCGA | AGCTTCCAAA | TGTTTGAAAA | TGAGATCATC | ACCAAGCTGG | 3420 |
| ATCATGAAGT | CGAAGGAGGC | AGAGGAGACG | AACAGTACAA | AGTGTTATTT | GATAAAATCC | 3480 |
| TTCTGGAACA | CTGCAGGAAG | CACAAATACC | TCGCCAAAAC | AGGAGAAACT | TTTGTAAAAC | 3540 |
| TCGTTGTGCG | CTTAATGGAA | AGGCTTTTGG | ATTATAGAAC | CATCATGCAC | GACGAGAACA | 3600 |
| AAGAAACCG | CATGAGCTGC | ACCGTCAATG | TGCTGAATTT | CTACAAAGAA | ATTGAAAGAG | 3660 |
| AAGAAATGTA | TATAAGGTAT | TTGTACAAGC | TCTGTGACCT | GCACAAGGAG | TGTGATAACT | 3720 |
| ACACCGAAGC | GGCTTACACC | TTGCTTCTCC | ATGCAAAGCT | TCTTAAGTGG | TCGGAGGATG | 3780 |

-continued

```
TGTGTGTGGC CCACCTCACC CAGCGGGACG GGTACCAGGC CACCACGCAG GGACAGCTGA    3840
AGGAGCAGCT CTACCAGGAA ATCATCCACT ACTTCGACAA AGGCAAGATG TGGGAGGAGG    3900
CCATTGCCTT GGGCAAGGAG CTAGCCGAGC AGTATGAGAA CGAAATGTTT GATTATGAGC    3960
AACTCAGCGA ATTGCTGAAA AAACAGGCTC AGTTTATGA AAACATCGTC AAAGTGATCA     4020
GGCCCAAGCC TGACTATTTT GCTGTTGGCT ACTACGGACA AGGGTTCCCC ACATTCCTGC    4080
GGGGAAAAGT TTTCATTTAC CGAGGGAAAG AGTATGAGCC CCGGGAAGAT TTTGAGGCTC    4140
GGCTCTTAAC TCAGTTTCCA AACGCCGAGA AAATGAAGAC AACATCTCCA CCAGGCGACG    4200
ATATTAAAAA CTCTCCTGGC CAGTATATTC AGTGCTTCAC AGTGAAGCCC AAACTCGATC    4260
TGCCTCCTAA GTTCACAGG CCAGTGTCAG AGCAGATTGT AAGTTTTAC AGGGTGAACG      4320
AGGTCCAGCG ATTTGAATAT TCTCGGCCAA TCCGGAAGGG AGAGAAAAAC CCAGACAATG    4380
AATTTGCGAA TATGTGGATC GAGAGAACCA TATATACAAC TGCATATAAA TTACCTGGAA    4440
TTTTAAGGTG GTTTGAGGTC AAGTCTGTTT TCATGGTGGA AATCAGCCCC CTGGAGAATG    4500
CCATCGAGAC CATGCAGCTG ACGAACGACA AGATCAACAG CATGGTGCAG CAGCACCTGG    4560
ATGACCCCAG CCTGCCCATC AACCCGCTCT CCATGCTCCT GAACGGCATC GTGGACCCAG    4620
CTGTCATGGG GGCTTCGCA AACTACGAAA AGGCCTTCTT TACAGACCGG TACCTGCAGG     4680
AGCACCCTGA GGCCCATGAA AAGATCGAGA AGCTCAAGGA CCTGATTGCT TGGCAGATTC    4740
CTTTTCTGGC CGAAGGGATC AGAATCCATG GAGACAAAGT CACGGAGGCA CTGAGGCCGT    4800
TCCACGAGAG GATGGAGGCC TGTTTCAAAC AGCTGAAGGA AAAGGTGGAG AAAGAGTACG    4860
GCGTCCGAAT CATGCCCTCA AGTCTGGATG ATAGAAGAGG CAGCCGCCCC CGGTCCATGG    4920
TGCGGTCCTT CACGATGCCT TCCTCATCCC GCCCTCTGTC TGTGGCCTCT GTCTCTTCCC    4980
TCTCATCGGA CAGCACCCCC TCCAGACCAG GCTCCGACGG GTTTGCCCTG GAGCCTCTCC    5040
TGCCAAAGAA AATGCACTCC AGGTCCCAGG ACAAGCTGGA CAAGGATGAC CTGGAGAAGG    5100
AGAAGAAGGA CAAGAAGAAG GAAAAAAGGA ACAGCAAACA TCAAGAGATA TTTGAGAAAG    5160
AATTTAAACC CACCGACATT TCCCTGCAGC AGTCTGAGGC TGTGATCCTT TCGGAAACGA    5220
TAAGTCCCCT GCGGCCCCAG AGACCGAAGA GCCAGGTGAT GAACGTCATT GGAAGCGAAA    5280
GGCGCTTCTC GGTGTCCCCC TCGTCACCGT CCTCCCAGCA AACACCCCCT CCAGTTACAC    5340
CAAGAGCCAA GCTCAGCTTC AGCATGCAGT CGAGCTTGGA GCTGAACGGC ATGACGGGGG    5400
CGGACGTGGC CGATGTCCCA CCCCCTCTGC CTCTCAAAGG CAGCGTGGCA GATTACGGGA    5460
ATTTGATGGA AAACCAGGAC TTGCTGGGCT CGCCAACACC TCCACCTCCC CCTCCACACC    5520
AGAGGCATCT GCCACCTCCA CTGCCCAGCA AAACTCCGCC TCCTCCCCCT CCAAAGACAA    5580
CTCGCAAGCA GACATCGGTG GACTCTGGGA TCGTGCAGTG ACATCGCAAG GCTCTCTGGA    5640
AAGAGTGTGC TGCCCCTCCC CATCTCCATG CCCTCTCCTT CTGTGTCCCC TGAGTCTGCT    5700
GTTTACCTCA TTGGGCCTGT GATGTTAACA TTTCGTGCGA CTGCTTTTTC TTCAAAGGAG    5760
TTCAGTTCTC ACCATGGAGT GAGTGGCCTT TAGCGTCATG GAGCAAGGTG GGTCTGGGAG    5820
GTAGATATGG GTCCGGGATG TGCCATCGTA GTTACCAGAG TTGGGGGCCT CTGAGTGTGT    5880
CTGGCTCTGA GAGAGTCTGA GTCTTGCCCA ACATTCTTT CTTTTTGTGC CAAATGACTT     5940
GCATTTGCAA AGAGCTCAAT TGCTCTGAGC TCAGCCAAGT AGGAGAGGCT AGGCCATCAC    6000
TCTTGGGAAG CTGTGTAGTG ATGATGTATA AGAATCCTCC TCACTGTCAT GGGATGTTGT    6060
ATCCAGCCCC TCCTTGTTCC AGCCGGTGGT GTGACTTCGT TGGTTGAGGT GTGTCTCCAA    6120
CCTACATCAG ACCATGAAGT TCAACCCCTC CAGGGAAGCT CCTGATTTCC CCTGCATAAT    6180
```

-continued

```
TGAAAATAGG ATATTCTCAG CTATTGAACA GTTACTAATT TATGGGGTGG AAACAGCATT    6240

AAGAATACTG AATCAAATGG AAAAACAAAT GAATACAGGA AGATAAGTGT TCGTTCTTTT    6300

CTGAAAAAAG AGTATGTGTA CCACAAGAGC TGGTTTTAAT TGGGTGAATT GTTTTGTCC     6360

TCATTCTGTA CAGAAATTTG TATATATGAT GGTTCTTAGA ACTTGTTTTA ATTTTTGTGG    6420

TCCTTCTGTT TATTATAATA GGCGTCCACC AATGATTATC CATATGTGTT CTTAATTTTT    6480

AACTGCTGGA AGTGTTAAAA CACACACACC CCGGAATTC                           6519
```

( 2 ) INFORMATION FOR SEQ ID NO:2:

( i ) SEQUENCE CHARACTERISTICS:
        ( A ) LENGTH: 1865 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL:

( i v ) ANTI-SENSE:

( v ) FRAGMENT TYPE:

( v i ) ORIGINAL SOURCE: spleen cell of homo sapiens ( x i ) SEQUENCE DESCRIPTION: SEQ ID NO:2:

```
Met Thr Arg Trp Val Pro Thr Lys Arg Glu Glu Lys Tyr Gly Val Ala
                 5                  10                 15

Phe Tyr Asn Tyr Asp Ala Arg Gly Ala Asp Glu Leu Ser Leu Gln Ile
            20                  25                  30

Gly Asp Thr Val His Ile Leu Glu Thr Tyr Glu Gly Trp Tyr Arg Gly
        35                  40                  45

Tyr Thr Leu Arg Lys Lys Ser Lys Lys Gly Ile Phe Pro Ala Ser Tyr
    50                  55                  60

Ile His Leu Lys Glu Ala Ile Val Glu Gly Lys Gly Gln His Glu Thr
65                  70                  75                  80

Val Ile Pro Gly Asp Leu Pro Leu Ile Gln Glu Val Thr Thr Thr Leu
                85                  90                  95

Arg Glu Trp Ser Thr Ile Trp Arg Gln Leu Tyr Val Gln Asp Asn Arg
            100                 105                 110

Glu Met Phe Arg Ser Val Arg His Met Ile Tyr Asp Leu Ile Glu Trp
        115                 120                 125

Arg Ser Gln Ile Leu Ser Gly Thr Leu Pro Gln Asp Glu Leu Lys Glu
    130                 135                 140

Leu Lys Lys Lys Val Thr Ala Lys Ile Asp Tyr Gly Asn Arg Ile Leu
145                 150                 155                 160

Asp Leu Asp Leu Val Val Arg Asp Glu Asp Gly Asn Ile Leu Asp Pro
                165                 170                 175

Glu Leu Thr Ser Thr Ile Ser Leu Phe Arg Ala His Glu Ile Ala Ser
            180                 185                 190

Lys Gln Val Glu Glu Arg Leu Gln Glu Glu Lys Ser Gln Lys Gln Asn
        195                 200                 205

Ile Asp Ile Asn Arg Gln Ala Lys Phe Ala Ala Thr Pro Ser Leu Ala
    210                 215                 220

Leu Phe Val Asn Leu Lys Asn Val Val Cys Lys Ile Gly Glu Asp Ala
225                 230                 235                 240

Glu Val Leu Met Ser Leu Tyr Asp Pro Val Glu Ser Lys Phe Ile Ser
```

-continued

|     |     |     | 245 |     |     |     |     | 250 |     |     |     | 255 |     |     |
| --- | --- | --- | --- | --- | --- | --- | --- | --- | --- | --- | --- | --- | --- | --- |
| Glu | Asn | Tyr | Leu | Val | Arg | Trp | Ser | Ser | Ser | Gly | Leu | Pro | Lys | Asp | Ile |
|     |     |     | 260 |     |     |     | 265 |     |     |     |     | 270 |     |     |
| Asp | Arg | Leu | His | Asn | Leu | Arg | Ala | Val | Phe | Thr | Asp | Leu | Gly | Ser | Lys |
|     |     |     | 275 |     |     |     | 280 |     |     |     |     | 285 |     |     |
| Asp | Leu | Lys | Arg | Glu | Lys | Ile | Ser | Phe | Val | Cys | Gln | Ile | Val | Arg | Val |
|     |     |     | 290 |     |     |     | 295 |     |     |     |     | 300 |     |     |
| Gly | Arg | Met | Glu | Leu | Arg | Asp | Asn | Thr | Arg | Lys | Leu | Thr | Ser | Gly |
| 305 |     |     |     |     | 310 |     |     |     | 315 |     |     |     |     | 320 |
| Leu | Arg | Arg | Pro | Phe | Gly | Val | Ala | Val | Met | Asp | Val | Thr | Asp | Ile | Ile |
|     |     |     |     | 325 |     |     |     |     | 330 |     |     |     |     | 335 |
| Asn | Gly | Lys | Val | Asp | Asp | Glu | Asp | Lys | Gln | His | Phe | Ile | Pro | Phe | Gln |
|     |     |     |     | 340 |     |     |     |     | 345 |     |     |     |     | 350 |
| Pro | Val | Ala | Gly | Glu | Asn | Asp | Phe | Leu | Gln | Thr | Val | Ile | Asn | Lys | Val |
|     |     |     |     | 355 |     |     |     |     | 360 |     |     |     |     | 365 |
| Ile | Ala | Ala | Lys | Glu | Val | Asn | His | Lys | Gly | Gln | Gly | Leu | Trp | Val | Thr |
|     |     |     |     | 370 |     |     |     |     | 375 |     |     |     |     | 380 |
| Leu | Lys | Leu | Leu | Pro | Gly | Asp | Ile | His | Gln | Ile | Arg | Lys | Glu | Phe | Pro |
| 385 |     |     |     |     | 390 |     |     |     | 395 |     |     |     |     | 400 |
| His | Leu | Val | Asp | Arg | Thr | Thr | Ala | Val | Ala | Arg | Lys | Thr | Gly | Phe | Pro |
|     |     |     |     | 405 |     |     |     |     | 410 |     |     |     |     | 415 |
| Glu | Ile | Ile | Met | Pro | Gly | Asp | Val | Arg | Asn | Asp | Ile | Tyr | Val | Thr | Leu |
|     |     |     |     | 420 |     |     |     |     | 425 |     |     |     |     | 430 |
| Val | Gln | Gly | Asp | Phe | Asp | Lys | Gly | Ser | Lys | Thr | Thr | Ala | Lys | Asn | Val |
|     |     |     |     | 435 |     |     |     |     | 440 |     |     |     |     | 445 |
| Glu | Val | Thr | Val | Ser | Val | Tyr | Asp | Glu | Asp | Gly | Lys | Arg | Leu | Glu | His |
|     |     |     | 450 |     |     |     |     | 455 |     |     |     | 460 |     |     |
| Val | Ile | Phe | Pro | Gly | Ala | Gly | Asp | Glu | Ala | Ile | Ser | Glu | Tyr | Lys | Ser |
| 465 |     |     |     |     | 470 |     |     |     | 475 |     |     |     |     | 480 |
| Val | Ile | Tyr | Tyr | Gln | Val | Lys | Gln | Pro | Arg | Trp | Phe | Glu | Thr | Val | Lys |
|     |     |     |     | 485 |     |     |     |     | 490 |     |     |     |     | 495 |
| Val | Ala | Ile | Pro | Ile | Glu | Asp | Val | Asn | Arg | Ser | His | Leu | Arg | Phe | Thr |
|     |     |     | 500 |     |     |     |     | 505 |     |     |     | 510 |     |     |
| Phe | Arg | His | Arg | Ser | Ser | Gln | Asp | Ser | Lys | Asp | Lys | Ser | Glu | Lys | Ile |
|     |     |     | 515 |     |     |     |     | 520 |     |     |     | 525 |     |     |
| Phe | Ala | Leu | Ala | Phe | Val | Lys | Leu | Met | Arg | Tyr | Asp | Gly | Thr | Thr | Leu |
|     |     |     | 530 |     |     |     | 535 |     |     |     |     | 540 |     |     |
| Arg | Asp | Gly | Glu | His | Asp | Leu | Ile | Val | Tyr | Lys | Ala | Glu | Ala | Lys | Lys |
| 545 |     |     |     |     | 550 |     |     |     | 555 |     |     |     |     | 560 |
| Leu | Glu | Asp | Ala | Ala | Thr | Tyr | Leu | Ser | Leu | Pro | Ser | Thr | Lys | Ala | Glu |
|     |     |     |     | 565 |     |     |     |     | 570 |     |     |     |     | 575 |
| Leu | Glu | Glu | Lys | Gly | His | Ser | Ala | Thr | Gly | Lys | Ser | Met | Gln | Ser | Leu |
|     |     |     |     | 580 |     |     |     |     | 585 |     |     |     |     | 590 |
| Gly | Ser | Cys | Thr | Ile | Ser | Lys | Asp | Ser | Phe | Gln | Ile | Ser | Thr | Leu | Val |
|     |     |     | 595 |     |     |     | 600 |     |     |     |     | 605 |     |     |
| Cys | Ser | Thr | Lys | Leu | Thr | Gln | Asn | Val | Asp | Leu | Leu | Gly | Leu | Leu | Lys |
|     |     |     | 610 |     |     |     | 615 |     |     |     |     | 620 |     |     |
| Trp | Arg | Ser | Asn | Thr | Ser | Leu | Leu | Gln | Gln | Asn | Leu | Arg | Gln | Leu | Met |
| 625 |     |     |     |     | 630 |     |     |     | 635 |     |     |     |     | 640 |
| Lys | Val | Asp | Gly | Gly | Glu | Val | Val | Lys | Phe | Leu | Gln | Asp | Thr | Leu | Asp |
|     |     |     |     | 645 |     |     |     |     | 650 |     |     |     |     | 655 |
| Ala | Leu | Phe | Asn | Ile | Met | Met | Glu | Asn | Ser | Glu | Ser | Glu | Thr | Phe | Asp |
|     |     |     |     | 660 |     |     |     |     | 665 |     |     |     |     | 670 |

```
Thr Leu Val Phe Asp Ala Leu Val Phe Ile Ile Gly Leu Ile Ala Asp
        675                 680                 685
Arg Lys Phe Gln His Phe Asn Pro Val Leu Glu Thr Tyr Ile Lys Lys
    690                 695                 700
His Phe Ser Ala Thr Leu Ala Tyr Thr Lys Leu Thr Lys Val Leu Lys
705                 710                 715                 720
Asn Tyr Val Asp Gly Ala Glu Lys Pro Gly Val Asn Glu Gln Leu Tyr
                725                 730                 735
Lys Ala Met Lys Ala Leu Glu Ser Ile Phe Lys Phe Ile Val Arg Ser
            740                 745                 750
Arg Ile Leu Phe Asn Gln Leu Tyr Glu Asn Lys Gly Glu Ala Asp Phe
        755                 760                 765
Val Glu Ser Leu Leu Gln Leu Phe Arg Ser Ile Asn Asp Met Met Ser
    770                 775                 780
Ser Met Ser Asp Gln Thr Val Arg Val Lys Gly Ala Ala Leu Lys Tyr
785                 790                 795                 800
Leu Pro Thr Ile Val Asn Asp Val Lys Leu Val Phe Asp Pro Lys Glu
                805                 810                 815
Leu Ser Lys Met Phe Thr Glu Phe Ile Leu Asn Val Pro Met Gly Leu
            820                 825                 830
Leu Thr Ile Gln Lys Leu Tyr Cys Leu Ile Glu Ile Val His Ser Asp
        835                 840                 845
Leu Phe Thr Gln His Asp Cys Arg Glu Ile Leu Leu Pro Met Met Thr
    850                 855                 860
Asp Gln Leu Lys Tyr His Leu Glu Arg Gln Glu Asp Leu Glu Ala Cys
865                 870                 875                 880
Cys Gln Leu Leu Ser His Ile Leu Glu Val Leu Tyr Arg Lys Asp Val
                885                 890                 895
Gly Pro Thr Gln Arg His Val Gln Ile Ile Met Glu Lys Leu Leu Arg
            900                 905                 910
Thr Val Asn Arg Thr Val Ile Ser Met Gly Arg Asp Ser Glu Leu Ile
        915                 920                 925
Gly Asn Phe Val Ala Cys Met Thr Ala Ile Leu Arg Gln Met Glu Asp
    930                 935                 940
Tyr His Tyr Ala His Leu Ile Lys Thr Phe Gly Lys Met Arg Thr Asp
945                 950                 955                 960
Val Val Asp Phe Leu Met Glu Thr Phe Ile Met Phe Lys Asn Leu Ile
                965                 970                 975
Gly Lys Asn Val Tyr Pro Phe Asp Trp Val Ile Met Asn Met Val Gln
            980                 985                 990
Asn Lys Val Phe Leu Arg Ala Ile Asn Gln Tyr Ala Asp Met Leu Asn
        995                 1000                1005
Lys Lys Phe Leu Asp Gln Ala Asn Phe Glu Leu Gln Leu Trp Asn Asn
    1010                1015                1020
Tyr Phe His Leu Ala Val Ala Phe Leu Thr Gln Glu Ser Leu Gln Leu
1025                1030                1035                1040
Glu Asn Phe Ser Ser Ala Lys Arg Ala Lys Ile Leu Asn Lys Tyr Gly
                1045                1050                1055
Asp Met Arg Arg Gln Ile Gly Phe Glu Ile Arg Asp Met Trp Tyr Asn
            1060                1065                1070
Leu Gly Gln His Lys Ile Lys Phe Ile Pro Glu Met Val Gly Pro Ile
        1075                1080                1085
Leu Glu Met Thr Leu Ile Pro Glu Thr Glu Leu Arg Lys Ala Thr Ile
    1090                1095                1100
```

```
Pro  Ile  Phe  Phe  Asp  Met  Met  Gln  Cys  Glu  Phe  His  Ser  Thr  Arg  Ser
1105                1110                1115                1120

Phe  Gln  Met  Phe  Glu  Asn  Glu  Ile  Ile  Thr  Lys  Leu  Asp  His  Glu  Val
               1125                1130                1135

Glu  Gly  Gly  Arg  Gly  Asp  Glu  Gln  Tyr  Lys  Val  Leu  Phe  Asp  Lys  Ile
          1140                1145                1150

Leu  Leu  Glu  His  Cys  Arg  Lys  His  Lys  Tyr  Leu  Ala  Lys  Thr  Gly  Glu
          1155                1160                1165

Thr  Phe  Val  Lys  Leu  Val  Val  Arg  Leu  Met  Glu  Arg  Leu  Leu  Asp  Tyr
     1170                1175                1180

Arg  Thr  Ile  Met  His  Asp  Glu  Asn  Lys  Glu  Asn  Arg  Met  Ser  Cys  Thr
1185                1190                1195                1200

Val  Asn  Val  Leu  Asn  Phe  Tyr  Lys  Glu  Ile  Glu  Arg  Glu  Glu  Met  Tyr
               1205                1210                1215

Ile  Arg  Tyr  Leu  Tyr  Lys  Leu  Cys  Asp  Leu  His  Lys  Glu  Cys  Asp  Asn
          1220                1225                1230

Tyr  Thr  Glu  Ala  Ala  Tyr  Thr  Leu  Leu  Leu  His  Ala  Lys  Leu  Leu  Lys
          1235                1240                1245

Trp  Ser  Glu  Asp  Val  Cys  Val  Ala  His  Leu  Thr  Gln  Arg  Asp  Gly  Tyr
     1250                1255                1260

Gln  Ala  Thr  Thr  Gln  Gly  Gln  Leu  Lys  Glu  Gln  Leu  Tyr  Gln  Glu  Ile
1265                1270                1275                1280

Ile  His  Tyr  Phe  Asp  Lys  Gly  Lys  Met  Trp  Glu  Glu  Ala  Ile  Ala  Leu
               1285                1290                1295

Gly  Lys  Glu  Leu  Ala  Glu  Gln  Tyr  Glu  Asn  Glu  Met  Phe  Asp  Tyr  Glu
          1300                1305                1310

Gln  Leu  Ser  Glu  Leu  Leu  Lys  Lys  Gln  Ala  Gln  Phe  Tyr  Glu  Asn  Ile
          1315                1320                1325

Val  Lys  Val  Ile  Arg  Pro  Lys  Pro  Asp  Tyr  Phe  Ala  Val  Gly  Tyr  Tyr
1330                1335                1340

Gly  Gln  Gly  Phe  Pro  Thr  Phe  Leu  Arg  Gly  Lys  Val  Phe  Ile  Tyr  Arg
1345                1350                1355                1360

Gly  Lys  Glu  Tyr  Glu  Pro  Arg  Glu  Asp  Phe  Glu  Ala  Arg  Leu  Leu  Thr
               1365                1370                1375

Gln  Phe  Pro  Asn  Ala  Glu  Lys  Met  Lys  Thr  Thr  Ser  Pro  Pro  Gly  Asp
               1380                1385                1390

Asp  Ile  Lys  Asn  Ser  Pro  Gly  Gln  Tyr  Ile  Gln  Cys  Phe  Thr  Val  Lys
          1395                1400                1405

Pro  Lys  Leu  Asp  Leu  Pro  Pro  Lys  Phe  His  Arg  Pro  Val  Ser  Glu  Gln
     1410                1415                1420

Ile  Val  Ser  Phe  Tyr  Arg  Val  Asn  Glu  Val  Gln  Arg  Phe  Glu  Tyr  Ser
1425                1430                1435                1440

Arg  Pro  Ile  Arg  Lys  Gly  Glu  Lys  Asn  Pro  Asp  Asn  Glu  Phe  Ala  Asn
               1445                1450                1455

Met  Trp  Ile  Glu  Arg  Thr  Ile  Tyr  Thr  Thr  Ala  Tyr  Lys  Leu  Pro  Gly
               1460                1465                1470

Ile  Leu  Arg  Trp  Phe  Glu  Val  Lys  Ser  Val  Phe  Met  Val  Glu  Ile  Ser
          1475                1480                1485

Pro  Leu  Glu  Asn  Ala  Ile  Glu  Thr  Met  Gln  Leu  Thr  Asn  Asp  Lys  Ile
     1490                1495                1500

Asn  Ser  Met  Val  Gln  Gln  His  Leu  Asp  Asp  Pro  Ser  Leu  Pro  Ile  Asn
1505                1510                1515                1520

Pro  Leu  Ser  Met  Leu  Leu  Asn  Gly  Ile  Val  Asp  Pro  Ala  Val  Met  Gly
```

|  |  |  |  |  | 1525 |  |  |  |  | 1530 |  |  |  |  | 1535 |  |
|---|---|---|---|---|---|---|---|---|---|---|---|---|---|---|---|---|
| Gly | Phe | Ala | Asn 1540 | Tyr | Glu | Lys | Ala | Phe 1545 | Phe | Thr | Asp | Arg | Tyr 1550 | Leu | Gln |
| Glu | His | Pro 1555 | Glu | Ala | His | Glu | Lys 1560 | Ile | Glu | Lys | Leu | Lys 1565 | Asp | Leu | Ile |
| Ala | Trp 1570 | Gln | Ile | Pro | Phe 1575 | Leu | Ala | Glu | Gly | Ile 1580 | Arg | Ile | His | Gly | Asp |
| Lys 1585 | Val | Thr | Glu | Ala | Leu 1590 | Arg | Pro | Phe | His 1595 | Glu | Arg | Met | Glu | Ala 1600 | Cys |
| Phe | Lys | Gln | Leu | Lys 1605 | Glu | Lys | Val | Glu 1610 | Lys | Glu | Tyr | Gly | Val 1615 | Arg | Ile |
| Met | Pro | Ser | Ser 1620 | Leu | Asp | Asp | Arg | Arg 1625 | Gly | Ser | Arg | Pro 1630 | Arg | Ser | Met |
| Val | Arg | Ser 1635 | Phe | Thr | Met | Pro | Ser 1640 | Ser | Ser | Arg | Pro 1645 | Leu | Ser | Val | Ala |
| Ser | Val 1650 | Ser | Ser | Leu | Ser | Ser 1655 | Asp | Ser | Thr | Pro | Ser 1660 | Arg | Pro | Gly | Ser |
| Asp 1665 | Gly | Phe | Ala | Leu | Glu 1670 | Pro | Leu | Leu | Pro | Lys 1675 | Lys | Met | His | Ser | Arg 1680 |
| Ser | Gln | Asp | Lys | Leu 1685 | Asp | Lys | Asp | Leu 1690 | Glu | Lys | Glu | Lys | Lys 1695 | Asp |  |
| Lys | Lys | Lys | Glu 1700 | Lys | Arg | Asn | Ser | Lys 1705 | His | Gln | Glu | Ile | Phe 1710 | Glu | Lys |
| Glu | Phe | Lys 1715 | Pro | Thr | Asp | Ile | Ser 1720 | Leu | Gln | Gln | Ser | Glu 1725 | Ala | Val | Ile |
| Leu | Ser 1730 | Glu | Thr | Ile | Ser | Pro 1735 | Leu | Arg | Pro | Gln | Arg 1740 | Pro | Lys | Ser | Gln |
| Val | Met 1745 | Asn | Val | Ile | Gly 1750 | Ser | Glu | Arg | Arg | Phe 1755 | Ser | Val | Ser | Pro | Ser 1760 |
| Ser | Pro | Ser | Ser | Gln 1765 | Gln | Thr | Pro | Pro 1770 | Pro | Val | Thr | Pro | Arg 1775 | Ala | Lys |
| Leu | Ser | Phe | Ser 1780 | Met | Gln | Ser | Ser | Leu 1785 | Glu | Leu | Asn | Gly | Met 1790 | Thr | Gly |
| Ala | Asp | Val 1795 | Ala | Asp | Val | Pro | Pro 1800 | Pro | Leu | Pro | Leu | Lys 1805 | Gly | Ser | Val |
| Ala | Asp 1810 | Tyr | Gly | Asn | Leu | Met 1815 | Glu | Asn | Gln | Asp | Leu 1820 | Leu | Gly | Ser | Pro |
| Thr 1825 | Pro | Pro | Pro | Pro | Pro 1830 | Pro | His | Gln | Arg | His 1835 | Leu | Pro | Pro | Pro | Leu 1840 |
| Pro | Ser | Lys | Thr | Pro 1845 | Pro | Pro | Pro | Pro 1850 | Lys | Thr | Thr | Arg | Lys 1855 | Gln |  |
| Thr | Ser | Val | Asp 1860 | Ser | Gly | Ile | Val | Gln 1865 |  |  |  |  |  |  |  |